(12) United States Patent
Yagi

(10) Patent No.: US 8,279,225 B2
(45) Date of Patent: Oct. 2, 2012

(54) ELEMENT MAPPING APPARATUS AND ELEMENT MAPPING IMAGE DISPLAY METHOD

(75) Inventor: Isao Yagi, Chiba (JP)

(73) Assignee: SII Nan Technology Inc. (JP)

( * ) Notice: Subject to any disclaimer, the term of this patent is extended or adjusted under 35 U.S.C. 154(b) by 440 days.

(21) Appl. No.: 12/544,586

(22) Filed: Aug. 20, 2009

(65) Prior Publication Data

US 2010/0045659 A1   Feb. 25, 2010

(30) Foreign Application Priority Data

Aug. 21, 2008   (JP) .................................. 2008-212994

(51) Int. Cl.
*G06T 11/20* (2006.01)
*G09G 5/00* (2006.01)

(52) U.S. Cl. ........... 345/440; 345/629; 250/306; 378/53

(58) Field of Classification Search ............. 250/442.11, 250/306; 378/53; 382/145; 345/440, 629
See application file for complete search history.

(56) References Cited

U.S. PATENT DOCUMENTS

| | | | |
|---|---|---|---|
| 2004/0228515 A1* | 11/2004 | Okabe et al. .................. | 382/145 |
| 2009/0045335 A1* | 2/2009 | Obara et al. .................. | 250/306 |
| 2009/0121152 A1* | 5/2009 | Obara et al. ............. | 250/442.11 |
| 2011/0031215 A1* | 2/2011 | Mantz et al. .................... | 378/53 |

FOREIGN PATENT DOCUMENTS

| | | |
|---|---|---|
| JP | 08-320298 A | 12/1996 |
| JP | 09-072868 A | 3/1997 |

\* cited by examiner

*Primary Examiner* — Chante Harrison
(74) *Attorney, Agent, or Firm* — Brinks Hofer Gilson & Lione

(57) ABSTRACT

Distribution images that are element mapping images displayed on a parent window of a display unit are switched by selecting a particular element or an analysis line to be displayed on a display element screen or a screen switch button using a keyboard or a mouse, so that the plural distribution images overlap to be overwritten at the same large size.

6 Claims, 6 Drawing Sheets

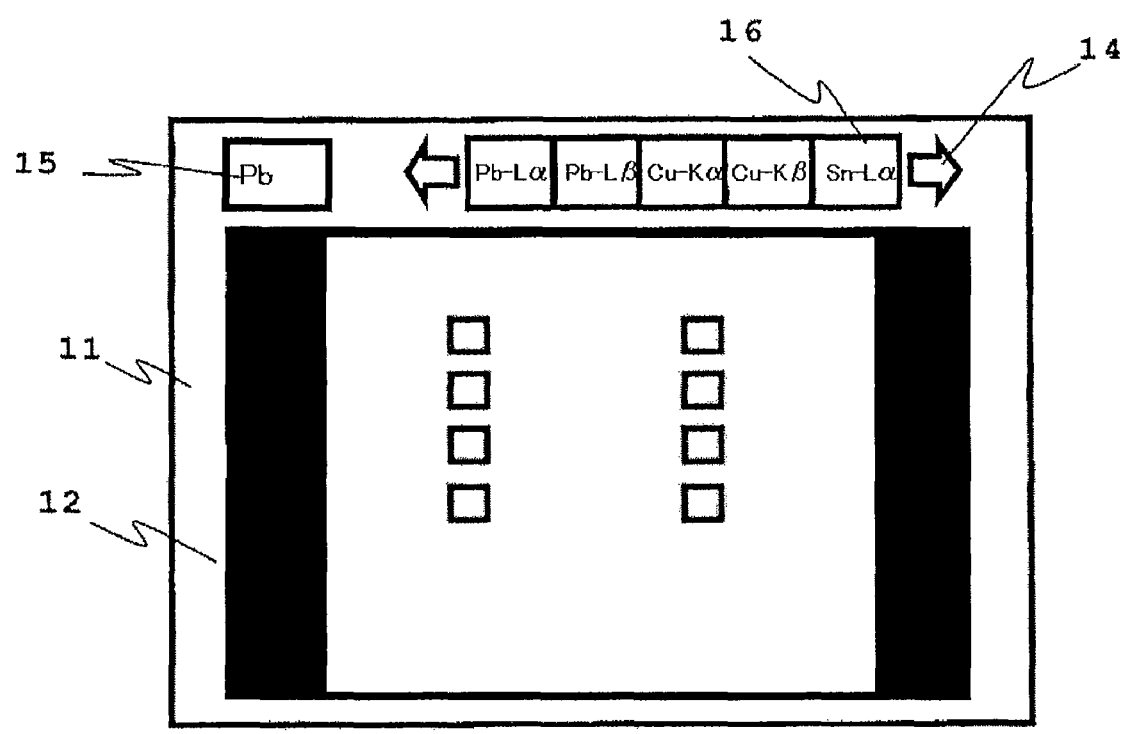
F I G. 4

ELEMENT MAPPING APPARATUS AND ELEMENT MAPPING IMAGE DISPLAY METHOD

RELATED APPLICATIONS

This application claims priority under 35 U.S.C. §119 to Japanese Patent Application No. JP2008-212994 filed on Aug. 21, 2008, the entire content of which is hereby incorporated by reference.

BACKGROUND OF THE INVENTION

1. Field of the Invention

The present invention relates to an element mapping apparatus and an element mapping image display method.

2. Description of the Related Art

An element mapping apparatus is an apparatus in which, for example, when an electron beam or an X-ray is irradiated on a small area of a sample by an electron beam source or an X-ray source, an characteristic X-ray such as a characteristic X-ray or a fluorescent X-ray emitted from the sample is detected by an X-ray detector, an analyzer such as a multichannel analyzer measures the energy intensity or counts the energy from the output of the X-ray detector to produce an energy spectrum, an element mapping image is obtained corresponding to a pixel position according to the kinds of elements or analysis lines, and the element mapping image is stored in an element mapping memory provided for each element as element mapping data, in order to display a distribution screen comprised of the element mapping images of a set element on an image display device such as a CRT as needed.

For example, when a sample containing arsenic (As) and lead (Pb) is irradiated with an electron beam, and the characteristic X-ray or the scattered X-ray emitted from the sample is detected by an X-ray detector, an example of an energy spectrum at an arbitrary point in the sample obtained by an analyzer is shown in FIG. 5. Here, the horizontal axis represents energy, and the vertical axis represents the intensities or counts of the detected characteristic X-ray and the like. On the basis of this, the concentration of particular elements can be measured.

In addition, in most cases, each element has plural analysis lines acting as peaks indicating characteristic X-ray energies, such as a Kα line, a Kβ line, an Lα line, and an Lβ line.

Therefore, the energy positions of the Kα line 23 of As and the Lα line 20 of Pb overlap with each other, and there is a problem in that Pb may be identified as As.

Therefore, when a peak exists in the energy position of the Lα line of Pb but peaks of the Lβ line 21 and Lγ line 22 in other energy positions of Pb do not exist, it is determined that Pb is not contained in the sample.

Similarly, when a peak of As does not exist in a position of Kβ line 24 although the peak of the Kα line 23 does exist, it is determined that As is not contained in the sample.

As described above, the peaks (analysis lines) of plural characteristic X-rays are compared for accurate qualitative analysis.

In addition, when two X-rays are incident on the X-ray detector at a short interval, in some cases, the two X-rays are not distinguished from each other but measured as a single X-ray. In this case, a phenomenon called sum peak occurs in which a peak having the energy of the sum of the two X-rays is observed in the energy spectrum.

Accordingly, there is a problem in that, for example, Au is identified as Cd, since the sum peak generated as the Lβ line of gold (Au) overlaps with the energy position of the Kα line of cadmium (Cd).

However, in the case of an element mapping image of a sample which is two-dimensionally measured, qualitative analysis using an energy spectrum at an arbitrary measurement position as described above cannot be performed. Therefore, distribution screens that are plural element mapping images are displayed to compare the effects of overlapping elements, such as the overlapping of the energy peaks, in order to perform element identification or quantitative analysis.

FIG. 6 shows a method of displaying element mapping images in an existing element mapping apparatus.

Using a mouse or a keyboard, an operator sets the size or the number of distribution screens 17 such as element mapping images to be displayed in a parent window 11 on a display that is an image display device of the element mapping apparatus, and sorts the distribution screens 17 to be arranged and displayed. In an example of the existing technique, the twelve distribution screens 17 are displayed in the parent window 11.

Accordingly, in the case where the existence of a target element in a sample is determined using the element distribution image, an element mapping image of plural energy bands is displayed, and this causes the effects of the overlapping elements to be considered. Therefore, accurate determination can be made (for example, refer to JP-A-9-72868).

In addition, as another existing technique, an element analysis image display method is known which overlaps distribution screens that are plural element mapping images obtained by element analysis over one another so as to display them on the same screen at the same time and thereby enable easy recognition of the relationship between 2D information (for example, refer to JP-A-8-320298).

However, the existing element mapping apparatus has the following problems.

In the case where plural distribution screens such as the element mapping images are displayed on the parent window at the same time to determine the existence of a target element, the number of distribution screens that can be displayed on the parent window is limited. In addition, when a number of distribution screens are displayed, the display size for each distribution screen is reduced. Therefore, there is a problem in that it is difficult to determine whether or not the same element is distributed at the same regions of the distribution screens. Moreover, when alternately observing an element displayed at other positions, there is a problem in that it is difficult to determine the distribution state of the same distribution screen.

In addition, in the case where the distribution screens are displayed at the same time on the same screen in order to determine existence of a target element and overlap one another, an intensity contrast obtained by changing color or brightness depending on the detection intensity of the data of each particular element is set to be displayed. However, in regard to a portion where plural image data overlap, when the degrees of overlap or the intensity contrasts obtained by changing brightness corresponding to the detection intensity are different depending on each pixel of the display screen, in order to display the original elements and the analysis lines of different energies of each element during the overlapping operation as different display colors, the combination of colors or the intensity contrast combination of the colors becomes complex, and there is a problem in that it is difficult to determine the distribution state of the distribution screen.

In consideration of the above-mentioned problems, an object of the invention is to provide an element mapping apparatus capable of significantly improving the visual quality for determining the difference between element distribution states of element mapping images, without limiting the number or reducing the size of distribution screens such as the element mapping images, thereby enabling correct recognition of the element distribution states.

SUMMARY OF THE INVENTION

In order to achieve the above-mentioned object, the following means are provided.

According to an aspect of the invention, there is provided an element mapping apparatus including: an excitation source that irradiates excitation particles such as an electron beam, light, or an X-ray on a sample; a detector that detects characteristic information of elements of the sample such as an electron beam, light, or an X-ray emitted from the sample; an analyzer that obtains the concentration or the intensity of each kind of element on the basis of the characteristic information to the elements; a data storage device that obtains and stores an element mapping image by matching the concentration or the intensity of each kind of element with a measured pixel position; and an image display device that displays the element mapping image, wherein the image display device arranges plural analysis screens comprised of plural element mapping images stored in the data storage device to overlap one another at the same size so as to display only one of the plural element mapping images on a parent window (parent screen) that is an image display range.

According to another aspect of the invention, there is provided an element mapping image display method including: irradiating excitation particles such as an electron beam, light, or an X-ray on a sample by an excitation source; detecting characteristic information to the elements of the sample, such as an electron beam, light, or an X-ray, emitted from the sample by a detector; obtaining the concentration or the intensity of each kind of element on the basis of the characteristic information to the elements by an analyzer; obtaining and storing an element mapping image by matching the concentration or the intensity of each kind of element with a measured pixel position by a data storage device; and arranging plural distribution screens (analysis screens) comprised of plural element mapping images stored in the data storage device to overlap one another at the same size by an image forming apparatus, and allowing only one of the plural element mapping images to be switched by an information processing unit so as to be displayed.

According to the element mapping apparatus and the element mapping image display method of the invention, there is no need to limit the number of or reduce the size of the analysis screens such as the element mapping images, and the visual quality for determining the difference between distribution states in the same region of the element mapping images is significantly improved. Therefore, there is a significant advantage in correctly recognizing the element distribution states.

BRIEF DESCRIPTION OF THE DRAWINGS

FIG. 4 is a diagram illustrating a second embodiment of the display screen of the element mapping apparatus applying the mapping image display method according to the invention.

DETAILED DESCRIPTION OF THE PREFERRED EMBODIMENTS

Hereinafter, exemplary embodiments of the invention will be described in detail with reference to the accompanying drawings.

Figure 1:
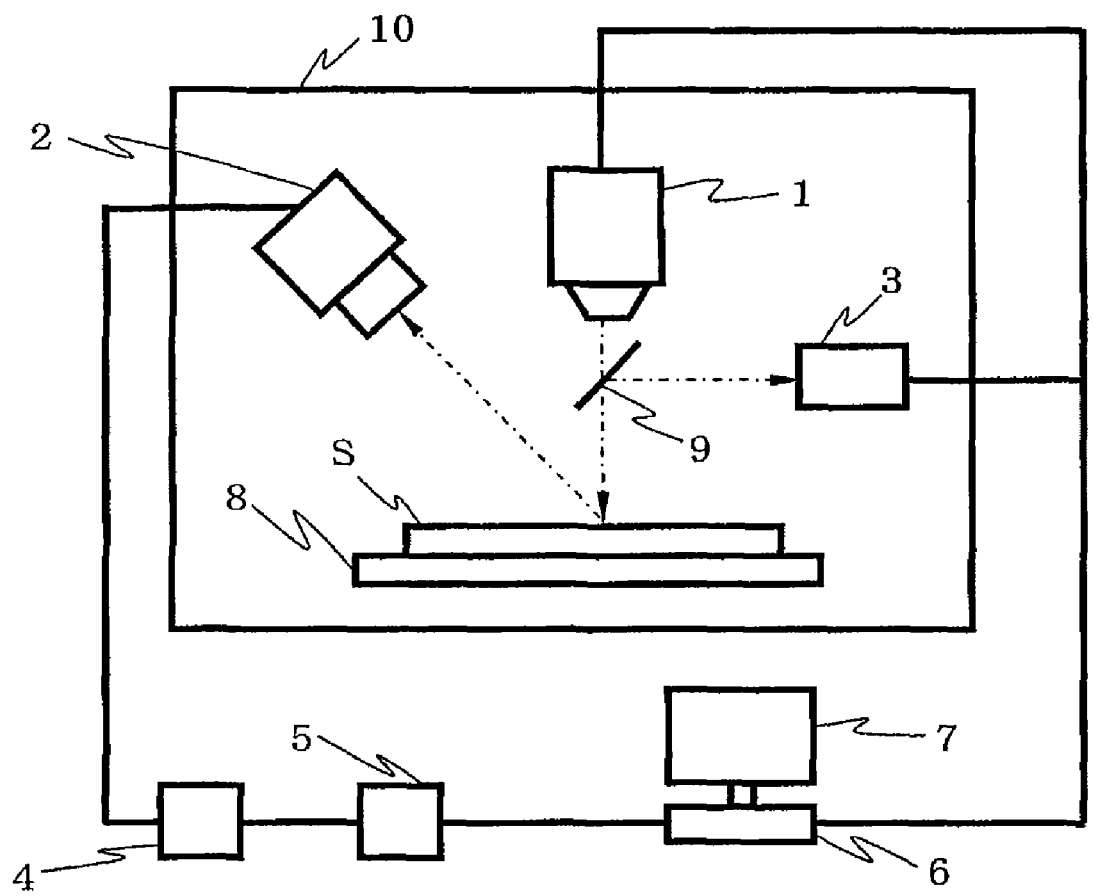
FIG. 1 is a schematic view illustrating an example of the configuration of an element mapping apparatus applying an analysis image display method according to the invention.

FIG. 1 is a schematic view illustrating an example of the configuration of an element mapping apparatus applying an analysis image display method (element mapping image display method) according to the invention.

The apparatus includes a sample stage (movement mechanism) 8 on which a sample S is placed to be moved together, an X-ray source 1 (excitation source) for irradiating a primary X-ray on an arbitrary irradiation point of the sample S, an X-ray detector 2 (detector) for detecting a characteristic X-ray and a scattered X-ray emitted from the sample S and outputting a signal including the energy information of the characteristic X-ray and the scattered X-ray, an optical microscope 3 for acquiring an enlarged illumination image of the sample S illuminated by an illuminator not shown, as image data, a mirror 9 which transmits the primary X-ray provided by the X-ray source 1 and causes light reflected from the sample S to be directed into the optical microscope 3, an X-ray analyzer 4 (analyzer) which is connected to the X-ray detector 2 and performs analysis processing to determine X-ray intensities corresponding to particular elements on the basis of the signal from the X-ray detector 2, a data storage device 5 which is connected to the X-ray analyzer 4 and obtains concentrations corresponding to a pixel position according to kinds of elements using the X-ray intensities corresponding to the particular elements analyzed by the X-ray analyzer 4 and stores data on the element mapping image, and an information processing unit 6 which determines the intensity contrast by changing colors or brightness depending on the X-ray intensity of the data on each particular element stored in the data storage device 5 and displays an image of positions corresponding to the irradiation points on a display unit 7 (image display device).

The X-ray source 1 of this embodiment uses a mechanism in which thermal electrons generated from a filament (anode) in a tube are accelerated by a voltage applied between the filament (anode) and a target (cathode) and collide with W (tungsten), Mo (molybdenum), Rh (rhodium), and the like to emit an X-ray, and the X-ray is used as the primary X-ray passing through a window such as a beryllium foil.

The X-ray detector 2 includes a semiconductor detection element (not shown; for example, an Si (silicon) element which is a pin-structure diode) which is provided on an X-ray incident window. When one X-ray photon is incident, the X-ray detector 3 generates a current pulse corresponding to the X-ray photon. The instantaneous current value of this current pulse is proportional to the energy of the incident characteristic X-ray. In addition, the X-ray detector 3 is set to convert the current pulse generated in the semiconductor detection element into a voltage pulse to be amplified and output as a signal.

The X-ray analyzer 4 is a wave-height analyzer (multi-channel analyzer) for generating an energy spectrum by using the wave height of the voltage pulse obtained from the signal. The X-ray analyzer 4 determines the X-ray intensity corresponding to a particular element from the energy spectrum.

The data storage device 5 is a computer configured with a CPU and the like and functioning as a device for analysis processing and data storage. The data storage device 5 can store 2D images X-ray mapped using the energy spectrum received from the X-ray analyzer 4 and measurement position information on the basis of the energy spectrum.

The information processing unit 6 is a computer configured with a CPU and the like and functioning as a device. The information processing unit 6 has a function of displaying the 2D image (analysis screen) stored in the data storage device 5, in which the energy of the characteristic X-ray of elements is mapped, as an element mapping image on the display unit 7. The information processing unit 6 has functions of controlling the X-ray source 1 connected to the configuration and storing optical images from the optical microscope 3. The information processing unit 6 can display various types of information on the display unit 7 corresponding to the control.

Next, a mapping image display method used in the element mapping apparatus having the configuration of FIG. 1 will be described with reference to the accompanying drawing.

Figure 2:
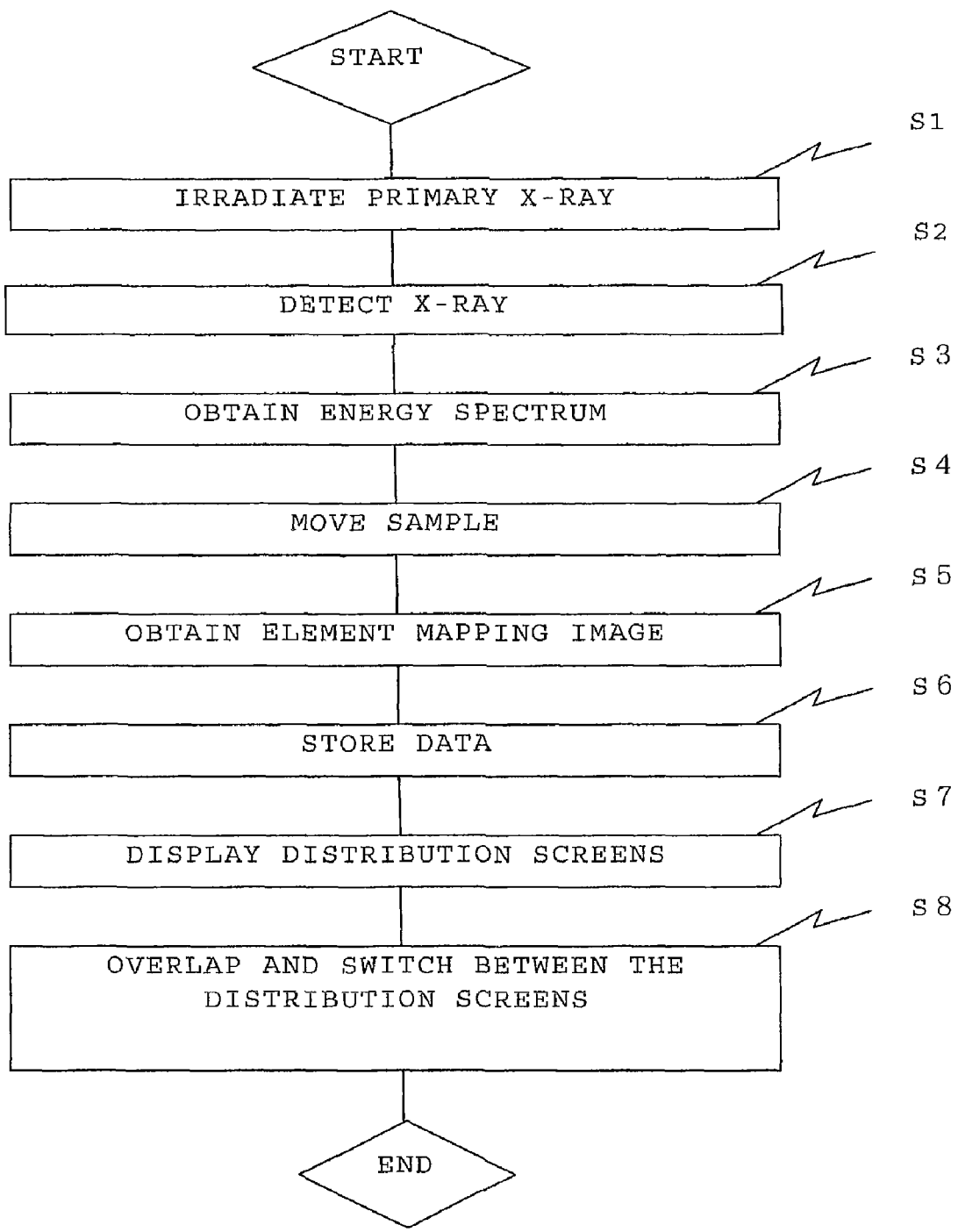
FIG. 2 is a flowchart illustrating an example of the analysis image display method according to the invention.

FIG. 2 is a flowchart illustrating a first embodiment of the mapping image display method according to the invention.

Figure 3:
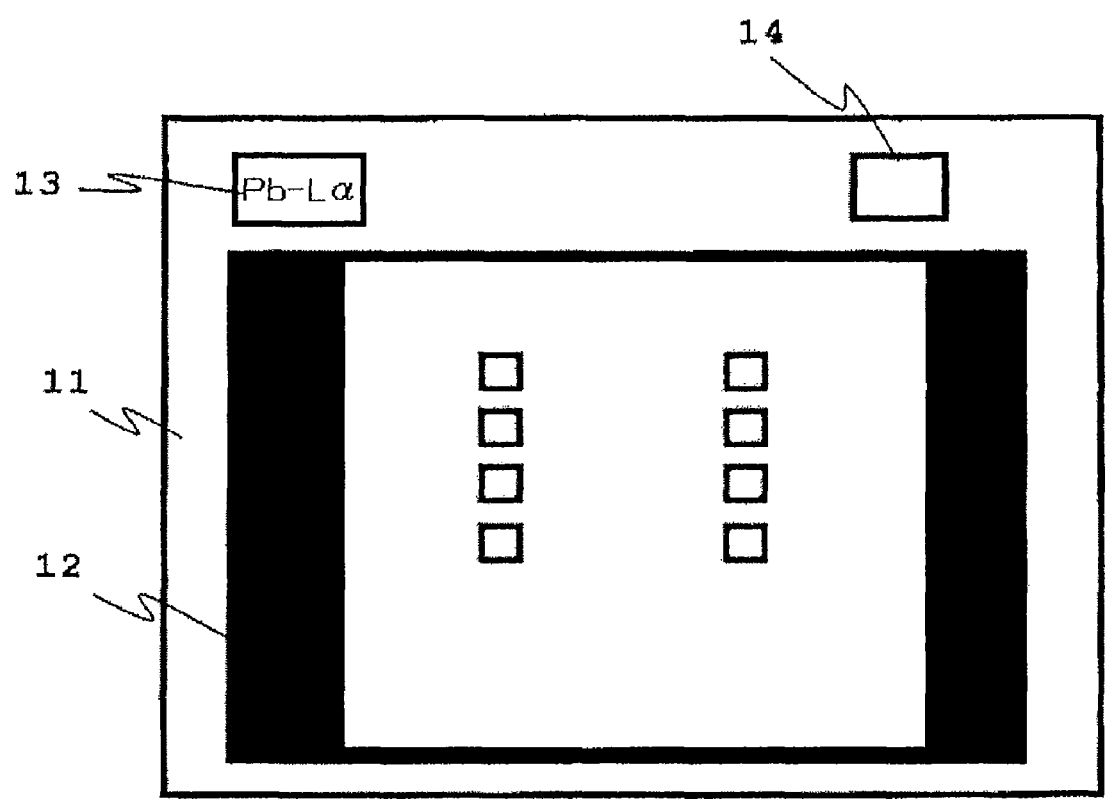
FIG. 3 is a diagram illustrating a first embodiment of a display screen of the element mapping apparatus applying the mapping image display method according to the invention.
Figure 5:
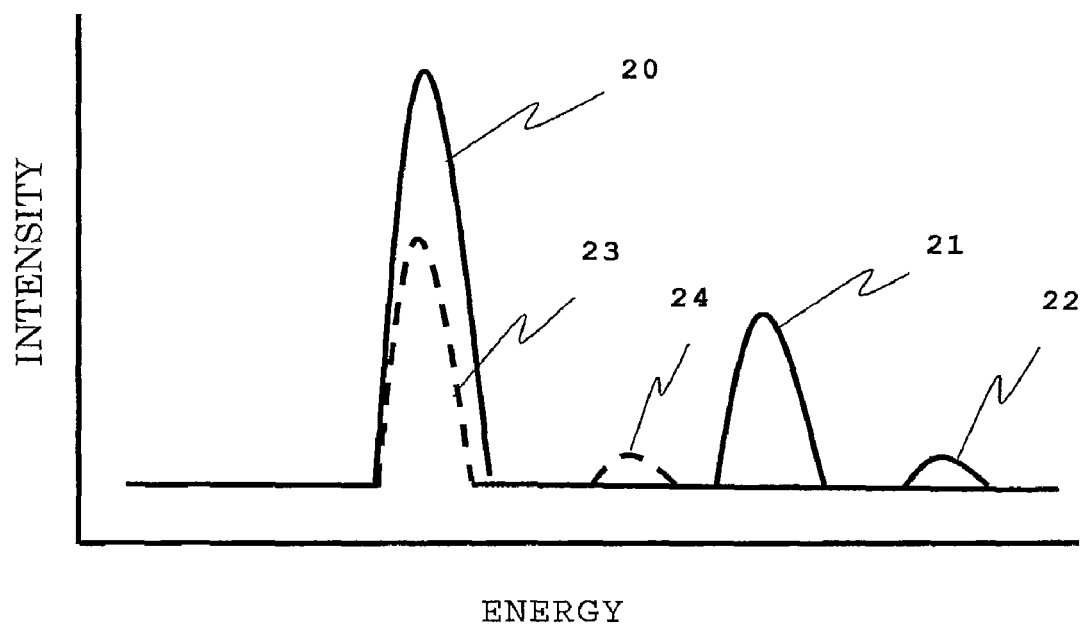
FIG. 5 is a diagram illustrating an example of an energy spectrum at an arbitrary position of a sample containing lead (Pb) and arsenic (As).
Figure 6:
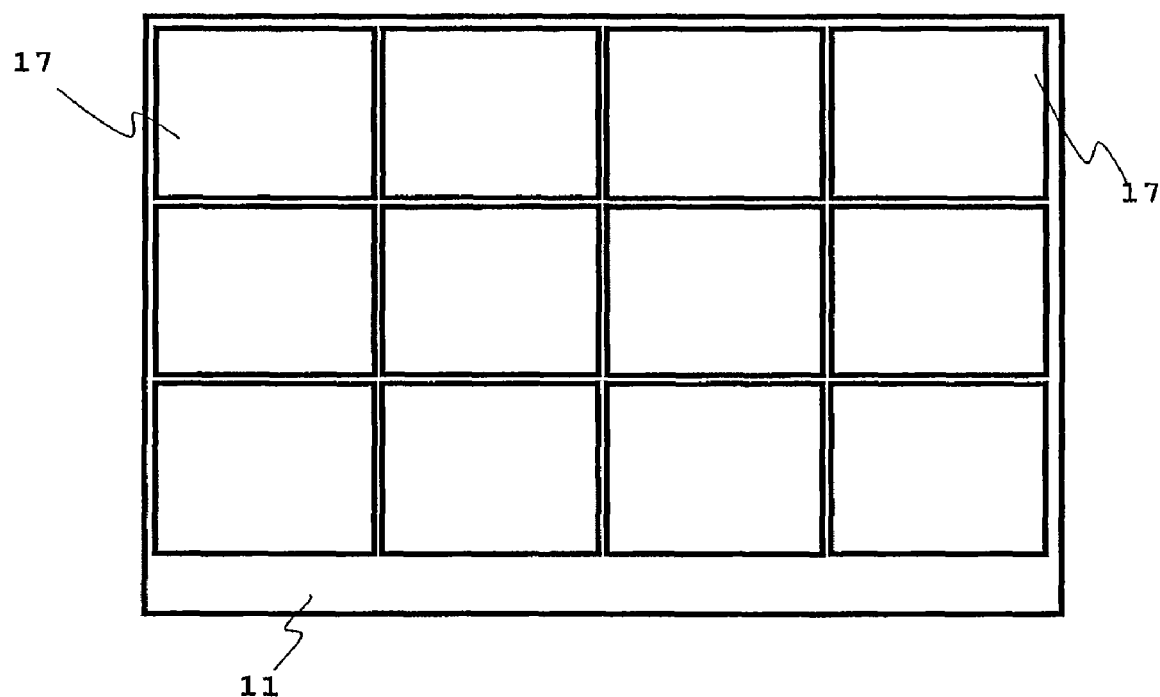
FIG. 6 is a diagram illustrating an example of a display screen for explaining an existing technique.

FIG. 3 is a diagram illustrating a first embodiment of a display screen of the element mapping apparatus applying the mapping image display method according to the invention.

The X-ray source 1 irradiates a primary X-ray on a predetermined measurement position of a sample S (S1). The X-ray detector 2 (detector) detects a characteristic X-ray and a scattered X-ray emitted from the sample S and outputs a signal including the energy information of the characteristic X-ray and the scatted X-ray (S2). Next, the X-ray analyzer 4 (analyzer), such as a multi-channel analyzer, selects and counts the energy output of the X-ray detector to generate an energy spectrum (S3). The sample S is moved to the next measurement position by the sample stage 8 (movement mechanism) (S4). Then, the X-ray analyzer 4 (analyzer) repeats the operations S1 to S4 to obtain an element mapping image as 2D information corresponding to each pixel position according to the types of elements or characteristic analysis lines thereof (S5). The data storage device 5 (element mapping memory) stores data on the energy spectrum of each measurement position and data on the element mapping images (S6). The information processing unit 6 determines the intensity contrast by changing colors or brightness depending on the X-ray intensity of the data for each particular element stored in the data storage device 5. The display unit 7 (image display device), such as a CRT, displays a distribution screen 12 as an element mapping image in a parent window 11 as a distribution screen 12 comprised of an element mapping image of a designated particular element (S7). An input device (not shown) such as a mouse is used to switch between the distribution screens 12 through the information processing unit 6 by clicking a screen switch button 14 in order to sequentially correct (overwrite) the element mapping images of each of the particular elements with the same size to be displayed (S8). Here, whenever the distribution screen 12 is switched, a display element screen 13 showing the type of element and the type of analysis line displayed on the distribution screen 12 is switched.

For example, the distribution screens are switched in the order of Pb-Lα (Lα analysis line of Pb), Lβ, and Mα, and back to Lα.

Incidentally, in this embodiment, the distribution screen 12 that is the element mapping image displayed in the parent window 11 on the display unit 7 is configured to have a similar figure to a mapping region that is a measurement range set in advance.

FIG. 4 is a diagram illustrating a second embodiment of the display screen that can be obtained by the element mapping apparatus applying the mapping image display method according to the invention.

Here, a description of the same parts as those of the first embodiment is omitted.

In this embodiment, in regard to the distribution screen 12 of the element mapping image of each particular element stored in the data storage device 5, only the name of the particular element such as Pb and Sn is displayed on a display element screen 15, and the list of analysis lines such as Kα and Lα lines according to the name of the element is displayed on an image list screen 16. In addition, an input device (not shown) such as a mouse is used to switch between the distribution screens 12 through the information processing unit 6 by clicking the screen switch button 14 or directly clicking the image list screen 16 in order to select and sequentially correct (overwrite) the element mapping images of each of the particular elements with the same size to be displayed.

Specifically, each of the plural distribution screens 12 showing the element mapping images displayed in the parent window 11 of the display unit 7 is switched with another distribution screen having the same display size, and the element mapping images of the elements to be displayed and analysis lines related to the elements are switched to improve visual quality for displaying the difference between the element distribution states in the element mapping images with large size, thereby enabling correct identification of the element distribution states.

In addition, the information processing unit 6 may be set to display optical microscopic images of the sample S output from the optical microscope 3 as distribution screens 12 of the same size which can be switched, as in the case of the element mapping image that is an X-ray mapping 2D image.

Otherwise, the optical microscopic image may be displayed to overlap with the distribution screen 12 of the element mapping image that is the X-ray mapping 2D image.

In addition, in this embodiment, the image list screen 16 may display the types of elements and analysis lines such as Pb-Lα as a list of the distribution screens 12 of the element mapping images of each particular element in text, display a reduced screen of the element mapping image of each particular element, or simultaneously display the text and the reduced screen.

In addition, in this embodiment, only a single display element screen 15 is provided, and clicked to switch to a particular element to be displayed. However, similar to the image list screen of this embodiment, plural display element screens may be displayed.

In addition, plural particular elements or analysis lines are selected from the display element screen 15 and the image list screen 16 to be set, and plural element mapping images selected at a predetermined interval are sequentially displayed. Otherwise, plural element mapping images selected using an input device, such as the scroll bar of a mouse, are sequentially displayed.

Accordingly, it is not necessary to move viewpoint to view the selection screens, such as the element analysis screen and the analysis line selection screen, to switch the screen which is advantageous in that the difference between the element distribution states for each element mapping image can be correctly recognized.

The sample stage 8, the X-ray source 1, the X-ray detector 2, and the optical microscope 3 are housed in a sample chamber 10 which can be decompressed. At the time of measurement, the sample chamber 10 is decompressed so that the X-ray is not absorbed into the air, or substituted with predetermined gas after decompression.

In addition, the sample stage 8 is an XYZ stage which can move vertically and horizontally and whose height can be adjusted by a stepping motor (not shown) in a state where the sample S is fixed thereon. The sample stage 8 is controlled by the information processing unit 6 to move the irradiation point of the primary X-rays relative to the sample S in a mapping region that is a measurement range set in advance. Since the irradiation point of the primary X-rays is moved relative to the sample, the X-ray source or the X-ray detector may be moved instead of the sample stage.

In the element mapping apparatus of this embodiment, the X-ray source 1 is used as an excitation source to excite the sample to emit a characteristic X-ray and scattered X-ray. However, instead, an electron beam may also be used. In addition, instead of a combination of the X-ray detector 3 and the X-ray analyzer 4, a combination of an X-ray spectrometer, an X-ray detector, and a single channel analyzer may be used.

In addition, in the element mapping image apparatus of the invention, light such as a laser beam in addition to the X-ray or the electron beam may be used as the excitation source to use ions, electrons, X-rays, and light as detection particles ejected from the sample, which have the characteristic information to the elements. In addition, the apparatus can be applied to the following particle excitation analysis and the like.

Specifically, the element mapping image display method used in the element mapping image apparatus may be applied to various particle excitation analyses such as transmission electron microscopy, scanning electron microscopy, Auger electron spectroscopy, low-speed electron diffraction, electron probe microanalysis, Rutherford backscattering spectroscopy, secondary ion mass spectrometry, ion scattering spectroscopy, beam-foil spectroscopy, particle radiation excitation X-ray spectroscopy, ion (or the like) excitation emission spectroscopy, X-ray photoelectron spectroscopy, X-ray fluorescence spectrometry, X-ray diffractometry, and ultraviolet photoelectron spectroscopy.

What is claimed is:

1. An element mapping apparatus comprising:
   an excitation source that irradiates excitation particles on a sample;
   a detector that detects characteristic information of elements of the sample emitted from the sample;
   an analyzer that obtains the concentration of each kind of element on the basis of the characteristic information to the elements;
   a data storage device that obtains and stores an element mapping image by matching the concentration of each kind of element with a measured pixel position, the element mapping image comprising a first element mapping image for a first element and a first analysis line and a second element mapping image for a second element and a second analysis line, the first element mapping image depicting the sample with distribution of the first element with a predetermined view and the second element mapping image depicting the sample with distribution of the second element with the predetermined view, whereby information on the sample is obtained without disassembling the sample; and
   an image display device that displays distribution screens showing the element mapping image;
   wherein the distribution screens having the same size overlap with and are superimposed on one another, and the distribution screens are sequentially switched such that the first element mapping image is selected, displayed and overwritten by the second element mapping image whereby difference between element distribution states in the element mapping images can be recognized.

2. The element mapping apparatus according to claim 1, wherein the distribution screen shows plural analysis lines of the same element.

3. The element mapping apparatus according to claim 1, wherein the image display device sequentially switches between the distribution screens that are plural element mapping images selected at a predetermined time interval or by an input device so as to be displayed.

4. An element mapping image display method comprising:
   irradiating excitation particles on a sample by an excitation source;
   detecting characteristic information to the elements of the sample emitted from the sample by a detector;
   obtaining the concentration of each kind of element on the basis of the characteristic information to the elements by an analyzer;
   obtaining and storing an element mapping image by matching the concentration of each kind of element with a measured pixel position by a data storage device, the element mapping image comprising a first element mapping image for a first element and a first analysis line and a second element mapping image for a second element and a second analysis line, the first element mapping image depicting the sample with distribution of the first element with a predetermined view and the second element mapping image depicting the sample with distribution of the second element with the predetermined view, whereby information on the sample is obtained without disassembling the sample; and
   displaying one of a plurality of distribution screens showing the element mapping image, wherein displaying one of the distribution screens comprises:
   arranging the distribution screens having the same size to overlap with and be superimposed on one another; and
   sequentially switching between the distribution screens to display one distribution screen at a time such that the first element mapping image is selected, displayed and overwritten by the second element mapping image;
   whereby difference between element distribution states in the element mapping images can be recognized.

5. The element mapping image display method according to claim 4, wherein the distribution screen switches between plural analysis lines of the same element.

6. The element mapping image display method according to claim 4, wherein sequentially switching between the distribution screens comprises sequentially switching between the distribution screens at a predetermined time interval.

* * * * *

UNITED STATES PATENT AND TRADEMARK OFFICE
CERTIFICATE OF CORRECTION

PATENT NO. : 8,279,225 B2
APPLICATION NO. : 12/544586
DATED : October 2, 2012
INVENTOR(S) : Isao Yagi It is certified that error appears in the above-identified patent and that said Letters Patent is hereby corrected as shown below:

On the Title Page

Left column, item (73), replace "SII Nan Technology Inc." with --SII NanoTechnology Inc.--.

Signed and Sealed this
Twenty-second Day of April, 2014

Michelle K. Lee
*Deputy Director of the United States Patent and Trademark Office*